United States Patent [19]
Thyen et al.

[11] 3,985,227
[45] Oct. 12, 1976

[54] PACKAGE FOR ARMED SUTURES

[75] Inventors: Eberhard Thyen, Middlesex; Peter Komarnycky, Raritan, both of N.J.

[73] Assignee: Ethicon, Inc., Somerville, N.J.

[22] Filed: Nov. 5, 1975

[21] Appl. No.: 629,472

[52] U.S. Cl. .......................... 206/63.3; 206/44.12; 206/45.23; 206/227; 206/380; 206/492
[51] Int. Cl.² .......................................... A61L 17/02
[58] Field of Search ............ 206/63.3, 44.12, 45.18, 206/45.13, 45.21, 45.23, 227, 380, 370, 381, 382, 495, 492

[56] References Cited
UNITED STATES PATENTS

| | | | |
|---|---|---|---|
| 2,111,265 | 3/1938 | Heckel | 206/382 |
| 2,126,444 | 8/1938 | Bollinger, Jr. | 206/370 |
| 2,628,711 | 2/1953 | Flannery | 206/382 |
| 2,669,350 | 2/1954 | Railton | 206/45.21 |
| 2,692,676 | 10/1954 | Grover | 206/63.3 |
| 2,695,097 | 11/1954 | Easton | 206/45.21 |
| 3,014,582 | 12/1961 | McGrane | 206/380 |
| 3,180,487 | 4/1965 | Vooenborg | 206/227 |
| 3,206,018 | 9/1965 | Lewis et al. | 206/63.3 |
| 3,363,751 | 1/1968 | Shave et al. | 206/63.3 |
| 3,779,375 | 12/1973 | Foster | 206/63.3 |

Primary Examiner—William Price
Assistant Examiner—Bruce H. Bernstein
Attorney, Agent, or Firm—Wayne R. Eberhardt

[57] ABSTRACT

A one-piece folded suture package for a plurality of single or double-armed sutures comprising a front panel, a back panel and two inner panels. The sutures are individually mounted on the two inner panels with the needles at one end and the suture strand extending therefrom over the length of the panel and secured near the other end of the panel. The panels are offset in a vertical direction to expose the upper end of both inner panels and display the needles in two horizontal tiers. The sutures are removable from the package by grasping the needles and withdrawing the suture strand from between the panels of the package. The package is optionally provided with a cover flap to cover the needle display area and integral locking means to secure the package in its folded construction.

16 Claims, 6 Drawing Figures

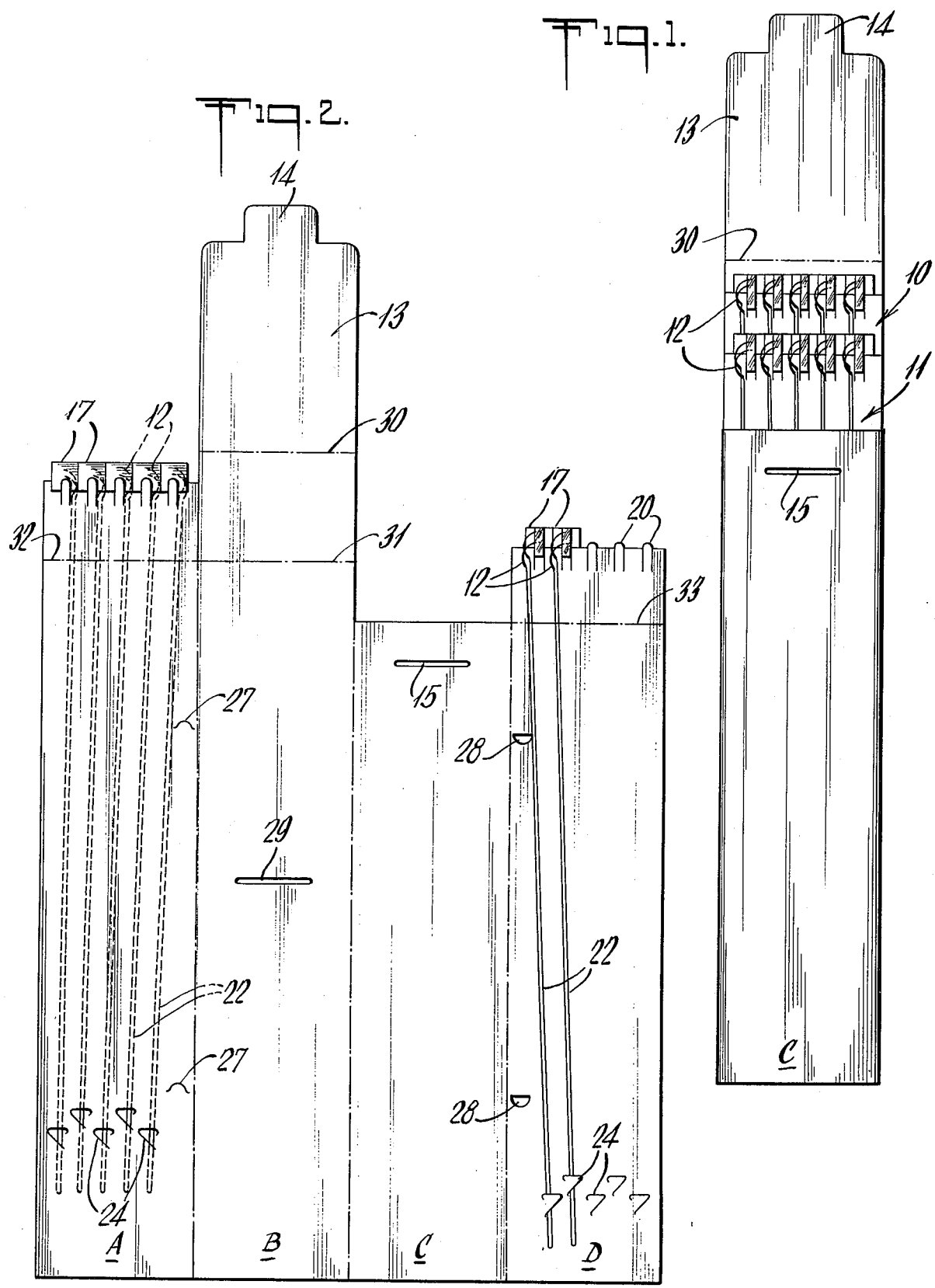

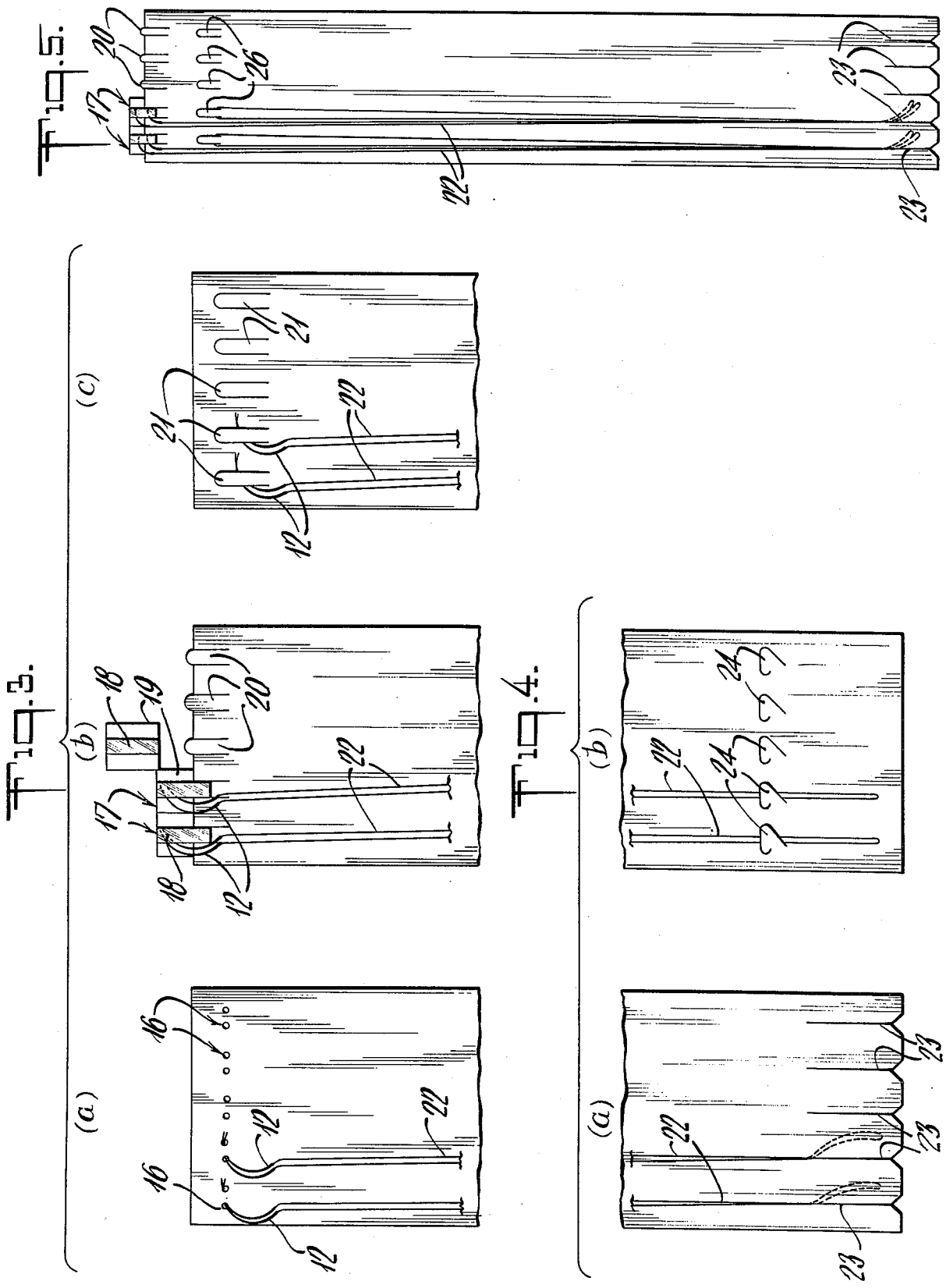

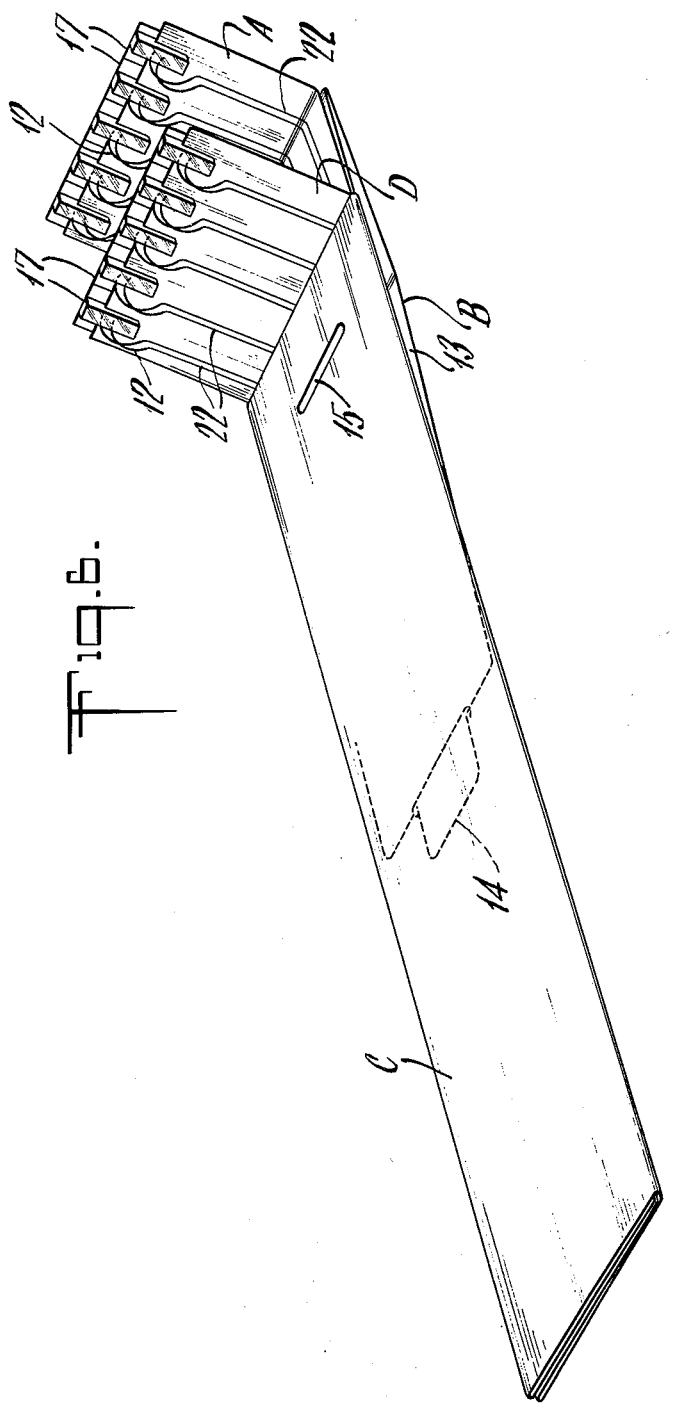

PACKAGE FOR ARMED SUTURES

BACKGROUND OF THE INVENTION

1. Field of the Invention

This invention relates to packages for surgical sutures, and more particularly to folded paper-board packages for holding and dispensing a plurality of individually mounted single or double-armed sutures.

2. Description of Prior Art

Packages for surgical sutures are constructed according to the nature of the suture and its intended use. In general, suture packages are constructed with the objective of making the suture readily available to the surgeon with a minimum of handling. This requires that the suture be packaged in a manner that allows the package to be opened and the suture to be removed with a minimum of effort and without entangling the suture with itself or adjacent sutures. It is also desirable that once removed, the suture has a minimum of bends, kinks or tendency to coil. In packaging sutures, it is desirable that the needles be easily accessible, and in the case of double-armed sutures, it is desirable that the needles of individual sutures be maintained as pairs so that the sutures are removable from the package by grasping either or both of the needles.

As used herein, the term "suture" shall mean elongated, thread-like strands suitable for suturing, ligating, or other surgical procedures, with or without needles attached. The term "single-armed suture" shall mean suture having a needle affixed to one end, while the term "double-armed suture" shall mean a suture having needles affixed to both ends. The term "suture strand" shall refer specifically to elongated thread-like portion of the suture.

Heretofore, armed sutures have been packaged in various ways intended to minimize formation of kinks, bends and coils. For example, double-armed sutures have been wound in the form of a figure eight and packaged according to U.S. Pat. No. 3,759,376. The package of this reference is particularly well suited for use with heavy or stiff suture materials, particularly those which tend to adopt a set configuration based on the form in which the suture is packaged.

The present invention is particularly well suited for packaging fine cardiovascular sutures which are characterized by a light, flexible suture material and small, curved needles. It is accordingly an object of the present invention to provide a method and package for mounting a plurality of armed sutures. It is a further object of this invention to provide a package for a plurality of double-armed cardiovascular sutures which provides for easy access to and removal of individual sutures. A yet further object of this invention is to provide a package for a plurality of armed sutures comprising a one-piece folded and self-locking construction. These and other objects will be apparent from the ensuing description and claims.

SUMMARY

A folded suture package for a plurality of single or double-armed sutures characterized in that each suture is individually mounted on one of two inner panels, the upper portions of which are exposed to display the suture needles in two horizontal tiers while the major part of the suture strand is enclosed between the panels of the package. An integral cover flap may be provided to enclose the needle display area. In one embodiment, the needles of each double-armed suture are embedded in a three-dimensional resilient polymeric block which is removable from the supporting panel and provides for the simultaneous removal of both needles with attached suture.

DESCRIPTION OF DRAWINGS

FIG. 1 is a plan view of a suture package of the present invention with the cover flap open to show the needle display.

FIG. 2 is a plan view of the package of FIG. 1 prior to folding.

FIG. 3 is a partial plan view of the top portion of three suture mounting panels having different needle mounting means.

FIG. 4 is a partial plan view of the bottom portion of two suture mounting panels having different suture strand restraining means.

FIG. 5 is a plan view of a suture mounting panel providing for a double length of suture strand.

FIG. 6 is a view in perspective of an open suture package with the sutures presented for use.

DESCRIPTION OF PREFERRED EMBODIMENTS

Suture packages of the present invention are characterized by one piece, four panel folded construction which provides a front cover panel, a back cover panel and two inner suture mounting panels. Each suture mounting panel is provided with needle mounting means near the top of the panel and with suture strand holding means near the bottom of the panel.

The panels are offset in a vertical direction so that the first suture mounting panel extends above the front cover panel and the second suture mounting panel extends above the first suture mounting panel, whereby the needles of the sutures mounted on each panel are displayed in two horizontal tiers to the front of the package. In a preferred embodiment, the back cover panel is provided with a cover flap adapted to fold forward over the three other panels and be secured to the front panel to cover the needle display area. When the package is opened for use, the cover flap is adapted to be folded backward and secured to the outside of the back panel to avoid interfering with the removal of sutures from the package.

The suture package is preferably constructed of a heavy weight relatively stiff paper or paperboard such as 5 point to 12 point solid bleached sulfate board. This paperboard is readily foldable and yet sufficiently strong and stiff to support the sutures and provide a relatively rigid package. Similarly folded material including plastics, foils, and laminates of these with each other or with paper can also be used with good results.

Referring now to FIGS. 1 and 2, FIG. 1 illustrates a 10 suture package of the present invention in its folded construction and with a plurality of double-armed sutures contained therein. Cover flap 13 is opened to reveal needle display areas 10 and 11 with 5 double-armed sutures mounted in each area.

FIG. 2 illustrates the package of FIG. 1 before folding and with four double-armed sutures mounted and in place. The folder is comprised of four panels designated A, B, C and D which are foldably connected on adjacent sides. End panels A and D are the suture mounting panels which are provided with needle mounting means 20 at the top of the panel and suture retaining means 24 near the bottom of the panel. Double-armed sutures are mounted on the panels prior to folding with needles 12 affixed in the needle-mounting means and suture 22 held by the suture retaining means. Panels A and D are optionally equipped with integral tab and slot locking means 27 and 28 respectively which interlock to hold the folder in its folded construction. Alternative securing means such as adhesives, tapes or staples may be utilized in place of the integral tab or slot locking means.

Panels B and C are provided with slots 29 and 15 respectively which are adapted to receive tab 14 of cover flap 13 when the suture package is in its folded construction. Slot 15 of panel C is adapted to receive tab 14 when cover flap 13 is folded forward along line 30 to cover the needle display area. Slot 29 of panel B is adapted to receive tab 14 when cover flap 13 is folded backward along line 31 to expose the needle display area. In its backward folded position, the cover flap is prevented from interfering with the removal of the sutures.

Details of various needle mounting means are illustrated in FIG. 3. In FIG. 3a the mounting means comprise two apertures 16 through which the needles are threaded. In FIG. 3b there is illustrated a preferred needle mounting means 17 comprising a resilient pierceable polymer block 18 mounted on a paperboard base 19 and slipped between a tongue and slot of a suture panel. The needles are inserted into the polymer block and the suture is removed from the package by grasping the polymer block with needles therein and withdrawing the combination from the package. This needle mounting means is described and claimed in copending U.S. patent application Ser. No. 501,372, which application is incorporated herein by reference. FIG. 3c illustrates an alternative needle-mounting means in which the needles are hooked behind tab 21 projecting from the mounting panel. Alternatively, the suture strand immediately adjacent the needle may be hooked behind tab 21.

Details of various suture strand retaining means are illustrated in FIG. 4. FIG. 4a shows a simple slot 23 extending from the base of the mounting panel with the suture end passed through the slot and retained therein. FIG. 4b illustrates a preferred suture retaining means wherein the end of the suture is held behind a laterally projecting triangular tab 24 having the base of the triangle oriented toward the needle mounting means. In this design, each suture is suitably retained to prevent tangling inside the package and yet each is easily released by a gentle pull on the needle end of the suture.

The suture packages of the present invention are necessarily sized to accommodate specific lengths of sutures. As is apparent from the suture mounting detail illustrated in FIG. 2, the distance from the needle mounting means to the suture restraining means on the suture mounting panel is approximately ½ the length of the double-armed suture so that the suture is folded once and restrained near its midpoint. In this mounting system, longer sutures require correspondingly longer packages. A variation of this mounting system, however, is illustrated in FIG. 5 where the length of the suture is approximately four times the length of the panel. In this mounting system, which is particularly useful for sutures exceeding 20 inches in length, the midpoint of the suture is held by tab 26 near the needles at the top of the mounting panel and the double loop of sutures at the quarter length point is held in slot 23. When the suture is withdrawn from the package, the loops release easily from retaining slot 23 and tab 26.

The suture packages of the present invention are preferably provided with fold lines 31, 32 and 33 as shown in FIG. 2 to facilitate the use of the package and the removal of sutures therefrom. In its closed position, cover flap 13 is folded forward along line 30 and tab 14 is inserted in slot 15 to hold the cover in its closed position. When the package is opened, cover 13 is folded backward along line 31 and tab 14 is inserted in slot 29 to hold the cover in its open position. Fold line 31 is preferably below the top edge of panel A so that when the cover flap is folded back, the needle display area of panel A projects above the package for easy access to and removal of the needles. The needle display of panels A and D are then folded forward so that when the package is placed upon a horizontal surface, the needle display portions of panel A and D project upward to present the needles for ready removal from the package as illustrated in FIG. 6.

While the preceding description has been directed primarily to packages containing double-armed sutures, it will be appreciated that single-armed sutures could be packaged in a like manner with the single needle mounted in the needle display area while the remainder of the suture is contained within the package. Panels A and D or the suture mounting blocks 17 may be color coded in a package containing different types of sutures. Many other variations of the present invention which nevertheless employ the four panel, one piece folded construction and double-tier needle display area which characterize the improved packages of the present invention will be apparent to those skilled in the art, and such variations are accordingly included in the scope of the present invention.

What is claimed is:

1. A one-piece folded suture package comprising a front panel, a first inner panel, a second inner panel and a back panel, said first and second inner panels having needle mounting means at the upper end thereof and suture strand retaining means at the lower end thereof corresponding in number to said needle mounting means, said first inner panel extending above the top of said front panel to expose said needle mounting means of said first inner panel, said second inner panel extending above the top of said first inner panel to expose said needle mounting means of said second inner panel, at least one armed suture comprising a suture strand having at least one needle affixed to an end thereof mounted on each of said inner panels with the needles of said sutures mounted on said needle mounting means and the strands of said sutures secured by said suture strand retaining means, and means for securing said package in said folded construction.

2. A package of claim 1 wherein said first and second inner panels are foldably connected to said front and back panels respectively and said front and back panels are foldably connected to each other, whereby said suture package is formed by folding said first and second inner panels inwardly over said front and back panels respectively, and thereafter folding said front and first inner panel inwardly over said back and second inner panel.

3. A package of claim 1 wherein said needle mounting means on said first and second inner panels comprise needle receiving apertures in said panels.

4. A package of claim 1 wherein said needle mounting means on said first and second inner panels comprise three-dimensional resilient pierceable polymeric blocks.

5. A package of claim 4 wherein said blocks are removably secured to said panels.

6. A package of claim 1 wherein said suture strand retaining means on said first and second inner panels comprise suture receiving tabs.

7. A package of claim 6 wherein said tabs are laterally projecting triangular tabs with the base of the triangle oriented toward the needle mounting means.

8. A package of claim 1 constructed of paper or paperboard.

9. A package of claim 1 wherein said first and second inner panels are provided with interlocking means to secure said package in said folded construction.

10. A package of claim 9 wherein said interlocking means comprise a tab and slot.

11. A package of claim 1 wherein said suture is a double-armed suture.

12. A one-piece folded suture package comprising a front panel, a first inner panel, a second inner panel and a back panel and means for securing said panels in a folded construction, said first and second inner panels having needle mounting means at the upper end thereof and suture restraining means at the lower end thereof corresponding in number to said needle mounting means, said first inner panel extending above the top of said front panel to expose said needle mounting means of said first inner panel, said second inner panel extending above the top of said first inner panel to expose said needle-mounting means of said second inner panel, at least one needle affixed to an end thereof mounted on each of said inner panels with the needles of said sutures mounted on said needle mounting means and the strands of said sutures secured by said suture strand retaining means, a cover flap extending from the top of said back panel and adapted to be folded over said first and second inner panels and said front panel, and means for securing said cover flap to said front panel to enclose the needle mounting means of said first and second inner panels, whereby when said cover flap is opened said needles are exposed for grasping to remove said needles and suture from said inner panels.

13. A package of claim 12 wherein said first and second inner panels are foldably connected to said front and back panels respectively and said front and back panels are foldably connected to each other, whereby said suture package is formed by folding said first and second inner panels inwardly over said front and back panels respectively, thereafter folding said front and first inner panel inwardly over said back and second inner panel, and thereafter folding said cover flap over said first and second inner panels and said front panel and securing said cover flap to said front panel.

14. A package of claim 12 wherein said cover flap is secured to said front panel by an interlocking tab and slot.

15. A package of claim 12 constructed of paper or paperboard.

16. A package of claim 12 wherein said suture is a double-armed suture.

* * * * *